(12) United States Patent
Chou

(10) Patent No.: US 11,034,187 B2
(45) Date of Patent: Jun. 15, 2021

(54) SMART WHEEL

(71) Applicant: Chun-Tao Chou, New Taipei (TW)

(72) Inventor: Chun-Tao Chou, New Taipei (TW)

( * ) Notice: Subject to any disclaimer, the term of this patent is extended or adjusted under 35 U.S.C. 154(b) by 503 days.

(21) Appl. No.: 15/990,128

(22) Filed: May 25, 2018

(65) Prior Publication Data

US 2019/0358997 A1 Nov. 28, 2019

(51) Int. Cl.
| | |
|---|---|
| *B60B 33/00* | (2006.01) |
| *B60B 23/10* | (2006.01) |
| *G05D 1/02* | (2020.01) |
| *G05D 1/00* | (2006.01) |
| *A61G 7/05* | (2006.01) |

(52) U.S. Cl.
CPC .......... *B60B 33/0028* (2013.01); *B60B 23/10* (2013.01); *B60B 33/0039* (2013.01); *G05D 1/0022* (2013.01); *G05D 1/0278* (2013.01); *A61G 7/0528* (2016.11); *B60B 2200/242* (2013.01); *B60B 2200/26* (2013.01)

(58) Field of Classification Search
CPC . B60B 33/0028; B60B 33/0039; B60B 23/10; G05D 1/0022; G05D 1/0278
See application file for complete search history.

(56) References Cited

U.S. PATENT DOCUMENTS

| | | | | |
|---|---|---|---|---|
| 6,491,127 B1* | 12/2002 | Holmberg | ............ | B60K 7/0007 180/21 |
| 6,786,559 B1* | 9/2004 | Kidd | .................... | A63C 17/223 301/5.23 |
| 7,761,954 B2* | 7/2010 | Ziegler | ................. | A47L 9/2857 15/320 |
| 7,866,453 B2* | 1/2011 | Wu | ........................ | A45C 5/145 190/18 A |
| 8,087,127 B2* | 1/2012 | Dayt | ................... | B60B 33/0073 16/47 |
| 8,240,410 B2* | 8/2012 | Heimbrock | .......... | A61G 1/0268 180/65.1 |
| 9,290,054 B2* | 3/2016 | Pfrenger | .............. | A01G 25/092 |
| 9,420,740 B2* | 8/2016 | Ishii | ..................... | B62D 11/003 |
| 10,434,820 B1* | 10/2019 | Savruha | ............. | B60B 33/0002 |
| 2007/0056141 A1* | 3/2007 | Armano | ............. | B60B 33/0073 16/35 R |
| 2009/0322492 A1* | 12/2009 | Hannah | .................. | G01C 21/00 340/10.5 |
| 2010/0155168 A1* | 6/2010 | Mies | ...................... | B60G 7/001 180/300 |
| 2010/0199458 A1* | 8/2010 | Yan | ..................... | B60B 33/0021 16/45 |
| 2013/0160237 A1* | 6/2013 | Shih | ...................... | B60B 33/025 16/47 |
| 2013/0326844 A1* | 12/2013 | Stoehr | ................ | B60B 33/0042 16/46 |
| 2015/0031269 A1* | 1/2015 | Kulich | ................. | A63H 17/262 446/457 |

(Continued)

*Primary Examiner* — Jason W San
(74) *Attorney, Agent, or Firm* — Muncy, Geissler Olds & Lowe, P.C.

(57) ABSTRACT

A smart wheel is provided, including a main body, at least one wheel body and a GPS module. The main body includes a pin and a wheel seat, and the wheel seat is connected with the pin. The at least one wheel body is pivoted to the wheel seat along an axial direction. The GPS module is arranged on the main body and includes a GPS chip.

7 Claims, 4 Drawing Sheets

(56) References Cited

U.S. PATENT DOCUMENTS

| | | | |
|---|---|---|---|
| 2015/0113766 A1* | 4/2015 | Hou | A45C 13/00 16/45 |
| 2015/0239290 A1* | 8/2015 | McKay | B62B 5/04 16/35 R |
| 2017/0349042 A1* | 12/2017 | Yang | B62D 7/026 |
| 2018/0099555 A1* | 4/2018 | Yang | B62D 5/0418 |
| 2019/0124820 A1* | 5/2019 | Dockter | B60B 33/0028 |

* cited by examiner

SMART WHEEL

BACKGROUND OF THE INVENTION

Field of the Invention

The present invention relates to a smart wheel.

Description of the Prior Art

Generally, in a hospital, wheel racks which are used to place expensive equipment or hospital beds are often moved to different places, for example, wards, operation rooms or laboratories. In order to track the positions of the wheel racks or hospital beds to prevent them from missing, a GPS module is arranged on the wheel rack or hospital bed, the GPS module sends a GPS signal wirelessly to a satellite or a control center to track the wheel rack or hospital bed and prevent samples or equipment from missing.

However, when some precision equipment is being used, there should be no wireless communication equipment around to prevent from interfering the precision of the equipment. If the GPS module is arranged on a rack of the wheel rack or hospital bed, the GPS module and the equipment interfere with each other, the GPS module is unable to send GPS signal effectively for position tracking, and the precision of the equipment is also affected.

The present invention has arisen to mitigate and/or obviate the afore-described disadvantages.

SUMMARY OF THE INVENTION

The major object of the present invention is to provide a smart wheel, which sends a GPS signal for tracking positions of wheel racks or hospital beds, and the GPS signal will not interfere with equipment placed on the wheel racks or hospital beds.

To achieve the above and other objects, a smart wheel is provided, including a main body, at least one wheel body and a GPS module. The main body includes a pin and a wheel seat, and the wheel seat is connected with the pin. The at least one wheel body is pivoted to the wheel seat along an axial direction. The GPS module is arranged on the main body and includes a GPS chip.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
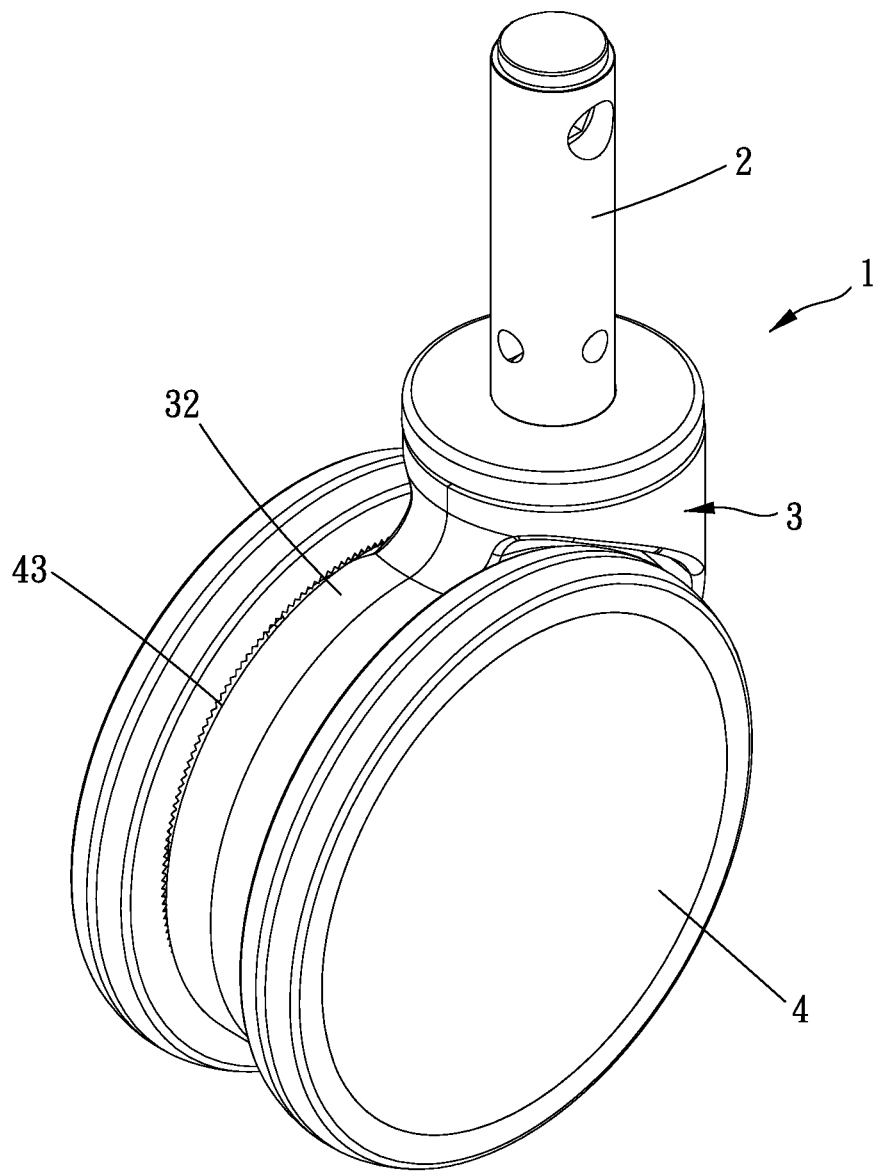
FIG. 1 is a stereogram of a preferred embodiment of the present invention.
Figure 2:
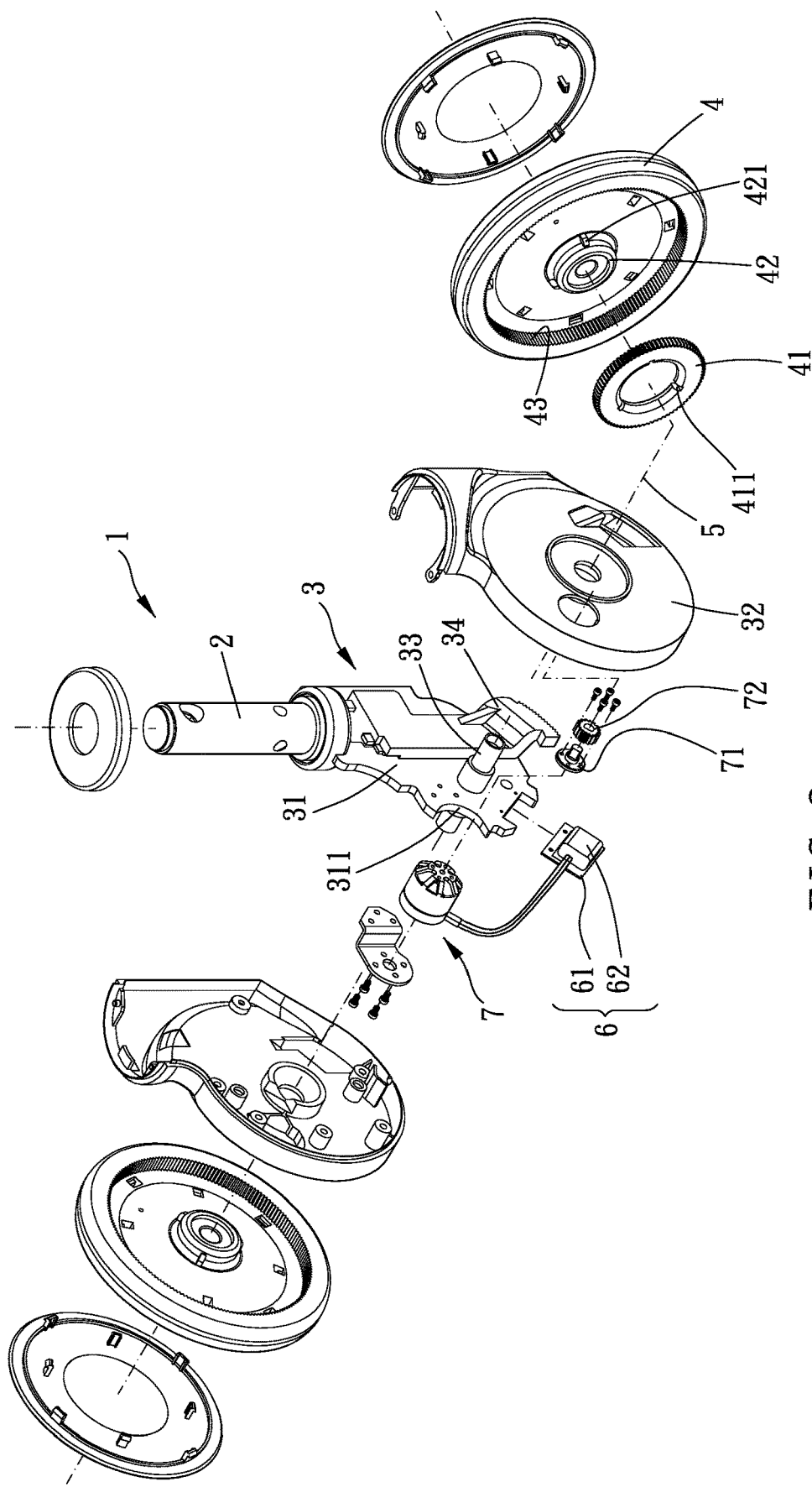
FIG. 2 is a breakdown view of the preferred embodiment of the present invention.
Figure 3:
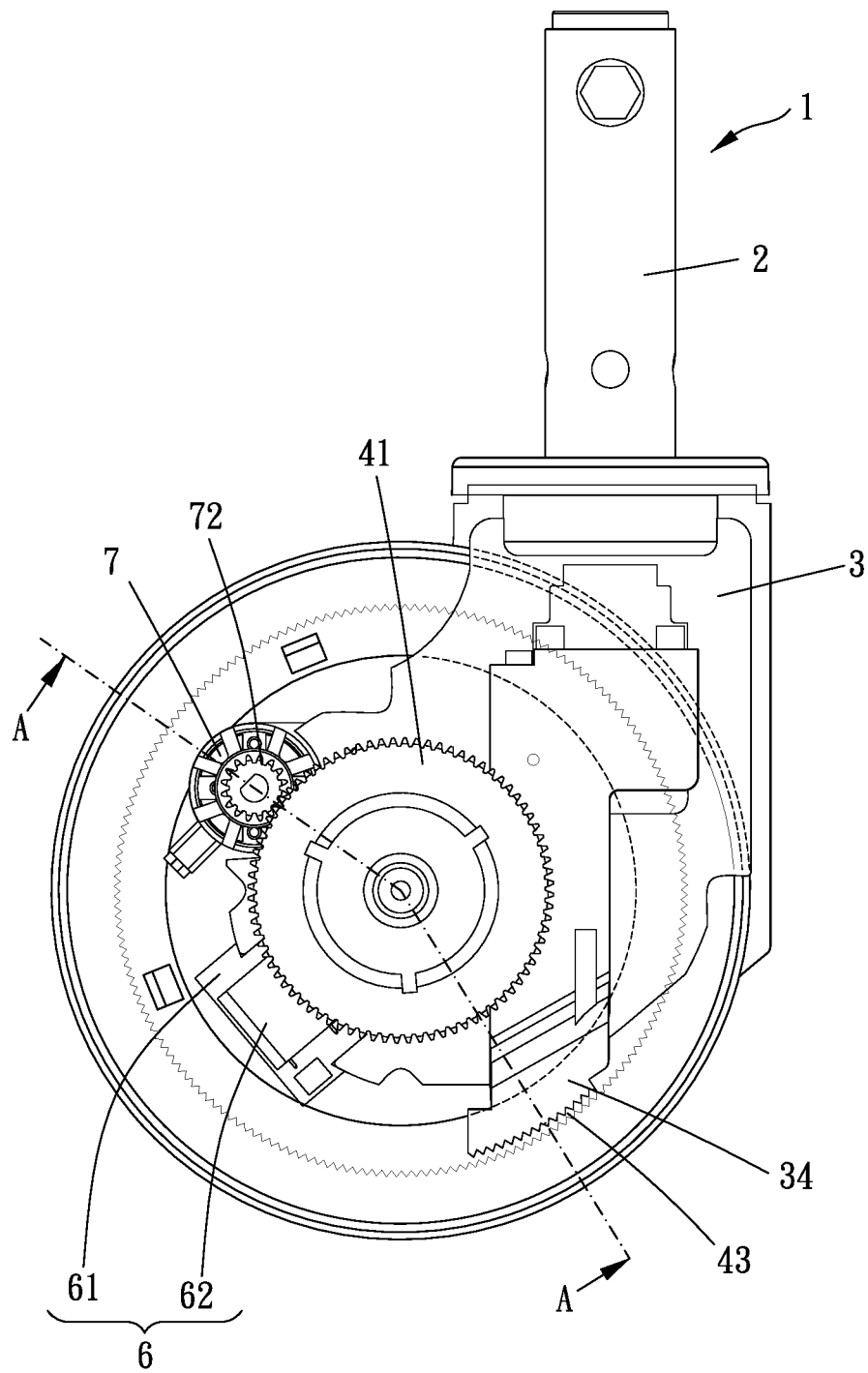
FIG. 3 is a cross-sectional side view of FIG. 1.
Figure 4:
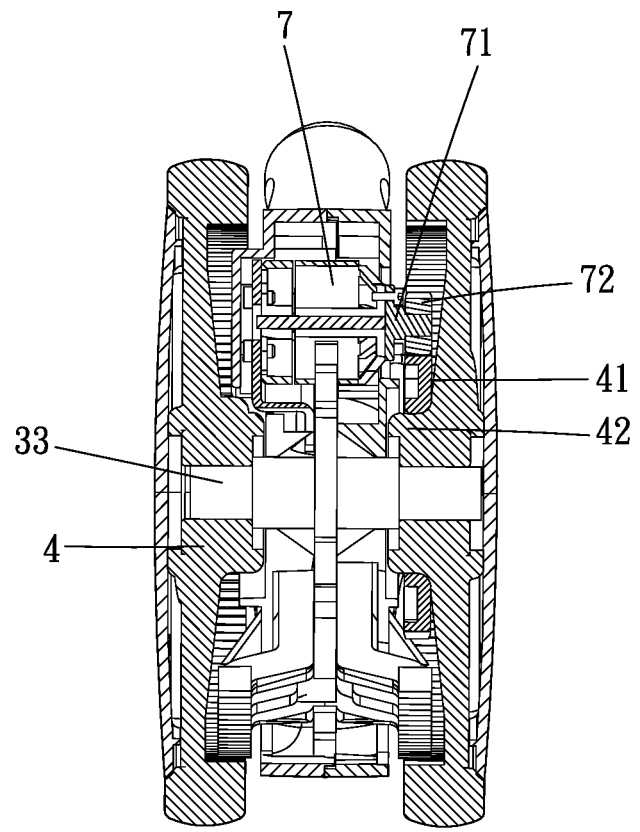
FIG. 4 is a cross-sectional view, taken along line A-A of FIG. 3.

Please refer to FIGS. 1 to 4 for a preferred embodiment of the present invention. A smart wheel includes a main body 1, at least one wheel body 4 and a GPS module 6.

The main body 1 includes a pin 2 and a wheel seat 3, and the wheel seat 3 is connected with the pin 2. In this embodiment, the main body 1 may be arranged on a wheeled stretcher (in other embodiment, it may be a wheel rack, a hospital bed or other objects) for an examination equipment placed thereon, but not limited thereto.

The at least one wheel body 4 is pivoted to the wheel seat 3 along an axial direction 5, and in this embodiment, a number of the at least one wheel body 4 is two.

The GPS module 6 is arranged on the main body 1 and includes a GPS chip 61, the GPS chip 61 sends a GPS signal to locate and track the smart wheel so as to know the position of the wheeled stretcher. Since the GPS module 6 is arranged on the main body 1, there is a distance between the GPS module 6 and the examination equipment so as to prevent from interfering with each other.

Specifically, the pin 2 and the wheel seat 3 are pivoted to each other along the axial direction 5 so that the wheeled stretcher can move forward and turn conveniently, and the GPS module 6 is arranged on the wheel seat 3.

In this embodiment, the GPS module 6 further includes an electricity storage unit 62, and the electricity storage unit 62 is electrically connected to the GPS chip 61 to provide electricity to the GPS chip 61 and prevent the GPS 61 from being inactive. In this embodiment, the electricity storage unit 62 is a capacitor to provide a small amount of electricity to the GPS chip 61; in other embodiments, the electricity storage unit 62 may be a battery having greater electricity capacity. In addition, the GPS chip 61 and the electricity storage unit 62 may be arranged in a box, and the box may be arranged on the main body 1 to protect the GPS module 6.

In addition, the smart wheel further includes an electricity generation assembly 7, the electricity generation assembly 7 is electrically connected to the GPS module 6, the electricity generation assembly 7 is arranged on the main body 1 and rotatably connected to one of the at least one wheel body 4 in such a manner that rotation of the wheel body 4 drives the electricity generation assembly 7 to generate electricity. Therefore, when the wheeled stretcher is pushed to move, the electricity generation assembly 7 is driven by the wheel body 4 to generate electricity and provide electricity to the GPS module 6. Even if the GPS module 6 does not have the electricity storage unit 62, when the wheeled stretcher moves to make the wheel body 4 rotate, the electricity generation assembly 7 is driven by the wheel body 4 to generate electricity and transmits electricity to the GPS module 6 so that the GPS module 6 can sends the GPS signal to know the moving path and instant position of the wheeled stretcher. Hence, the GPS module 6 does not need to be charged through an exterior power source.

Specifically, the wheel body 4 has a first gear 41, the electricity generation assembly 7 has a rotor 71 and a second gear 72 which link up with each other, and the first gear 41 is meshed with the second gear 42. In this embodiment, the wheel body 4 has an annular protrusion 42 along the axial direction 5, the annular protrusion 42 has at least one first restricting portion 421 along a radial direction thereof, the first gear 41 is circular and sleeved on the annular protrusion 42, and the first gear 41 has at least one second restricting portion 411 which is engaged with the first restricting portion 421 so as to make the first gear link up and rotate with the wheel body 4. In this embodiment, the annular protrusion 42 and the first gear 41 respectively have the plurality of first restriction portions 421 and the plurality of the second restricting portions 411 which correspond to each other, and when the first gear rotates, the second gear 72 and the rotor 71 are driven to rotate to make the electricity generation assembly 7 generate electricity.

It is to be noted that, in the embodiment, the electricity storage unit 62 is electrically connected to the GPS chip 61, the GPS chip 61 and the electricity storage unit 62 are arranged on a base plate 31, and the electricity generation assembly 7 is electrically connected to the electricity storage unit 62; therefore, when the electricity generation assembly 7 generates electricity and transmits electricity to the electricity storage unit 62, the electricity storage unit 62 transmits a small amount of electricity to the GPS chip 61. When the wheeled stretcher moves, the electricity storage unit 62 transmits a small amount of electricity to the GPS chip 61 to make the GPS chip 61 to send the GPS signal to track and record the position of the wheeled stretcher; and when the wheeled stretcher stops moving, the electricity generation assembly 7 does not continue to generate electricity. After a while, when the electricity of the electricity storage unit 62 is used up, the GPS chip 61 stops sending the GPS signal, and the GPS chip 61 will send the GPS signal again when the wheeled stretcher moves so as to effectively prevent the GPS signal from causing interference, save electricity and prevent the GPS chip 61 from overuse.

More specifically, the wheel seat 3 includes the base plate 31 and two shells 32, the two shells 32 cover on two sides of the base plate 31 along the axial direction 5, the base plate 31 has a recess 311 along a radial direction thereof, and the electricity generation assembly 7 is arranged on the recess 311. The wheel seat 3 further includes a wheel shaft 33, the wheel shaft 33 is disposed through the base plate 31 and the two shells 32 along the axial direction 5, and the two wheel bodies 4 are assembled to the wheel shaft 33, and the two shells 32 are located between the two wheel bodies 4.

In addition, in this embodiment, each of the at least one wheel body 4 has a ring groove 43, the wheel seat 3 has two brake shoes 34 which are slidable along a longitudinal direction of the pin 2, and the two brake shoes 34 are frictionally abuttable against the ring groove 43 to brake so as to prevent each of the two wheel bodies 4 from rotate randomly and prevent the wheeled stretcher from sliding randomly.

Given the above, in the smart wheel, the GPS chip sends the GPS signal to locate and track the smart wheel to the position of the wheeled stretcher, and since the GPS module is arranged on the main body, there is a distance between the GPS module and the examination equipment so as to prevent from interfering with each other.

In addition, the electricity generation assembly is arranged on the main body and connected one of the two wheel bodies to make the wheel body to rotate to drive the electricity generation assembly to generate electricity, and the electricity generation assembly is electrically connected to the GPS module; therefore, when the wheeled stretcher is pushed to move, the electricity generation assembly is driven by the wheel body and generates electricity to provide electricity to the GPS module. Hence, the GPS module does not need to be charged through an exterior power source.

While we have shown and described various embodiments in accordance with the present invention, it should be clear to those skilled in the art that further embodiments may be made without departing from the scope of the present invention.

What is claimed is:

1. A smart wheel, including:
   a main body, including a pin and a wheel seat, the wheel seat being connected with the pin;
   at least one wheel body, pivoted to the wheel seat along an axial direction;
   a GPS module, arranged on the main body and including a GPS chip;
   an electricity generation assembly, the electricity generation assembly being electrically connected directly to the GPS module, the electricity generation assembly being arranged on the main body and rotatably connected to one of the at least one wheel body in such a manner that rotation of the wheel body drives the electricity generation assembly to generate electricity to be supplied to the GPS chip;
   wherein the GPS module further includes an electricity storage unit, the electricity storage unit is electrically connected to the GPS chip, and the electricity storage unit is a capacitor transmits a small amount of electricity to the GPS chip;
   wherein the wheel body has a first gear, the electricity generation assembly has a rotor and a second gear which link up with each other, and the first gear is meshed with the second gear;
   wherein after the wheel body stops rotating and the electricity generation assembly does not continue to generate electricity for a while and the electricity of the electricity storage unit is used up, the GPS chip stops sending the GPS signal, and the GPS chip sends the GPS signal again when the wheel body rotates again.

2. The smart wheel of claim 1, wherein the pin and the wheel seat are pivoted to each other along the axial direction, and the GPS module is arranged on the wheel seat.

3. The smart wheel of claim 1, wherein the wheel body has an annular protrusion along the axial direction, the annular protrusion has at least one first restricting portion along a radial direction thereof, the first gear is circular and sleeved on the annular protrusion, and the first gear has at least one second restricting portion which is engaged with the first restricting portion.

4. The smart wheel of claim 1, wherein the GPS module further includes an electricity storage unit, the electricity storage unit is electrically connected to the GPS chip, the GPS chip and the electricity storage unit are arranged on a base plate, and the electricity generation assembly is electrically connected to the electricity storage unit.

5. The smart wheel of claim 1, wherein the wheel seat includes a base plate and two shells, the two shells cover on two sides of the base plate along the axial direction, the base plate has a recess along a radial direction thereof, and the electricity generation assembly is arranged on the recess.

6. The smart wheel of claim 5, wherein the wheel seat further includes a wheel shaft, the wheel shaft is disposed through the base plate and the two shells along the axial direction, a number of the at least one wheel body is two, the two wheel bodies are assembled to the wheel shaft, and the two shells are located between the two wheel bodies.

7. The smart wheel of claim 1, wherein each of the at least one wheel body has a ring groove, the wheel seat has two brake shoes which are slidable along a longitudinal direction of the pin, and the two brake shoes are frictionally abuttable against the ring groove.

<p style="text-align:center">* * * * *</p>